United States Patent
Verghese et al.

(10) Patent No.: US 11,039,886 B2
(45) Date of Patent: Jun. 22, 2021

(54) LIGHT BASED SKIN TREATMENT DEVICE

(71) Applicant: KONINKLIJKE PHILIPS N.V., Eindhoven (NL)

(72) Inventors: Babu Verghese, Eindhoven (NL); Rieko Verhagen, Vught (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/473,658

(22) PCT Filed: Dec. 27, 2017

(86) PCT No.: PCT/EP2017/084655
§ 371 (c)(1),
(2) Date: Jun. 26, 2019

(87) PCT Pub. No.: WO2018/122270
PCT Pub. Date: Jul. 5, 2018

(65) Prior Publication Data
US 2019/0328455 A1 Oct. 31, 2019

(30) Foreign Application Priority Data
Dec. 28, 2016 (EP) .................................... 16207164

(51) Int. Cl.
*A61B 18/20* (2006.01)
*A61B 5/00* (2006.01)
*A61B 18/00* (2006.01)

(52) U.S. Cl.
CPC .......... *A61B 18/203* (2013.01); *A61B 5/0095* (2013.01); *A61B 5/4836* (2013.01); *A61B 5/0059* (2013.01); *A61B 2018/0047* (2013.01)

(58) Field of Classification Search
CPC ........ A61B 18/203; A61B 2018/00452; A61B 2018/0047; A61B 5/0059; A61B 5/0095;
(Continued)

(56) References Cited

U.S. PATENT DOCUMENTS 7,282,060 B2    10/2007  DeBenedictis
9,414,888 B2 *  8/2016   Liu .................... A61B 18/20
(Continued)

FOREIGN PATENT DOCUMENTS

CN        105067568 A       11/2015
WO        WO0242719 A2      5/2002
(Continued)

OTHER PUBLICATIONS

PCT International Search Report, International application No. PCT/EP2017/084648, dated Apr. 4, 2018.
(Continued)

*Primary Examiner* — Jonathan T Kuo (57) ABSTRACT

A pulsed laser skin treatment device is for laser induced optical breakdown of hair or skin tissue. A feedback system is used for detecting a feedback system based on light and/or sound/and/or contact force or pressure. The feedback signal is used to determine whether a pulse was in the tissue or outside the tissue. With these data an effectiveness of the treatment can be determined which can be provided to a user.

15 Claims, 3 Drawing Sheets

(58) Field of Classification Search
CPC ....... A61B 5/4836; A61B 18/20–18/28; A61N 5/06–2005/073
See application file for complete search history.

(56) References Cited

U.S. PATENT DOCUMENTS

| | | |
|---|---|---|
| 2004/0040379 A1 | 3/2004 | O'Donnell |
| 2004/0043081 A1 | 3/2004 | Ye |
| 2008/0319430 A1* | 12/2008 | Zenzie ................. A61B 18/203 606/9 |
| 2009/0248004 A1* | 10/2009 | Altshuler ............... A61B 18/18 606/33 |
| 2012/0123444 A1 | 5/2012 | Verhagen |
| 2012/0283710 A1* | 11/2012 | Liu ....................... A61N 5/0616 606/9 |
| 2012/0283711 A1 | 11/2012 | Harvey |
| 2015/0038953 A1 | 11/2015 | Verhese |
| 2015/0328045 A1 | 11/2015 | Kurtz |
| 2016/0074116 A1* | 3/2016 | Varghese ............. A61B 18/203 606/9 |

FOREIGN PATENT DOCUMENTS

| | | |
|---|---|---|
| WO | WO2005011510 A1 | 2/2005 |
| WO | WO2008001284 A2 | 1/2008 |
| WO | WO2008089344 A2 | 7/2008 |
| WO | WO2014113574 A1 | 7/2014 |
| WO | WO 2014147543 A1 * | 9/2014 |
| WO | WO 2014174010 A1 * | 10/2014 |
| WO | WO 2015150460 A1 * | 10/2015 |
| WO | WO2015177750 A1 | 11/2015 |

OTHER PUBLICATIONS

Habbema L. et al., "Efficacy of minimally Invasive Nonthermal Laser-Induced Optical Breakdown Technology for Skin Rejuvenation", Lasers in Medical Science 28 (3), 935-940 (2013).

Habbema L. et al., "Minimally Invasive Non-Thermal Laser Technology Using Laser-Induced Optical Breakdown for Skin Rejuvenation," Journal of Biophotonics 5 (2), 194-199 (2012).

* cited by examiner

LIGHT BASED SKIN TREATMENT DEVICE

CROSS-REFERENCE TO PRIOR APPLICATIONS

This application is the U.S. National Phase application under 35 U.S.C. § 371 of International Application No. PCT/EP2017/084655, filed on Dec. 27, 2017, which claims the benefit of EP Patent Application No. EP 16207164.1, filed on Dec. 28, 2016. These applications are hereby incorporated by reference herein.

FIELD OF THE INVENTION

The invention pertains to a device and method for treatment of tissue of a subject by laser induced optical breakdown (LIOB). The device and method make use of focusing of a light beam through a light exit window which can be but need not be for contacting the tissue when the device is in use.

BACKGROUND OF THE INVENTION

Such light based skin treatment devices can be e.g., used for skin rejuvenation, wrinkle treatment and hair cutting. In light based wrinkle treatment, the device creates a focal spot in a dermis layer of the skin to be treated. The power and pulse duration of the laser and the dimension of the focal spot are selected such that a laser induced optical breakdown (LIOB) phenomenon affects the skin in order to stimulate re-growth of skin tissue and, therewith, to reduce wrinkles. In light based hair cutting, the light beam is focused inside the hair and the LIOB phenomenon causes the hair to be cut through.

For example, the international patent application published as WO 2005/011510 describes a device for shortening hairs comprising a laser source for generating a laser beam during a predetermined pulse time, an optical system for focusing the laser beam into a focal spot and a laser beam manipulator for positioning the focal spot in a target position. A dimension of the focal spot and a power of the generated laser beam are such that in the focal spot the laser beam has a power density which is above a characteristic threshold value for hair tissue above which, for the predetermine pulse time, a laser induced optical breakdown (LIOB) phenomenon occurs in the hair tissue.

In general, laser induced optical breakdown (LIOB) occurs in media, which are transparent or semi-transparent for the wavelength of the laser beam, when the power density ($W/cm^2$) of the laser beam in the focal spot exceeds a threshold value which is characteristic for the particular medium. Below the threshold value, the particular medium has relatively low linear absorption properties for the particular wavelength of the laser beam. Above the threshold value, the medium has strongly non-linear absorption properties for the particular wavelength of the laser beam, which are the result of ionization of the medium and the formation of plasma. This LIOB phenomenon results in a number of mechanical effects, such as cavitation and the generation of shock waves, which damage the medium in positions surrounding the position of the LIOB phenomenon.

It has been found that the LIOB phenomenon can be used to break and shorten hairs growing from skin. Hair tissue is transparent or semi-transparent for wavelengths between approximately 500 nm and 2000 nm. For each value of the wavelength within this range, LIOB phenomena occur in the hair tissue at the location of the focal spot when the power density ($W/cm^2$) of the laser beam in the focal spot exceeds a threshold value which is characteristic for the hair tissue. Said threshold value is rather close to the threshold value which is characteristic for aqueous media and tissue and is dependent on the pulse time of the laser beam. In particular, the threshold value of the required power density decreases when the pulse time increases.

In order to achieve mechanical effects as a result of the LIOB phenomenon which are sufficiently effective so as to cause significant damage, i.e. at least initial breakage of a hair, a pulse time in the order of, for example, 10 ns suffices. For this value of the pulse time, the threshold value of the power density of the laser beam in the focal spot is in the order of $2*10^{10}$ $W/cm^2$. For the described pulse time and with a sufficiently small dimension of the focal spot obtained, for example, by means of a lens having a sufficiently large numerical aperture, this threshold value can be achieved with a total pulse energy of only a few tenths of a millijoule.

The effectiveness of optical breakdown for skin rejuvenation depends on several factors such as optical and structural properties of the skin, laser intensity in the focus, optical coupling etc. In many cases, the treatment depth can be different, depending on the thickness of stratum corneum and epidermis.

SUMMARY OF THE INVENTION

A problem which can arise is that because the LIOB treatment is intended to be in the dermis which is underneath the epidermis, it can be difficult to see whether a pulse has been effective and therewith treatment efficacy is difficult to estimate. Also, the exit window can be damaged by the products of the LIOB (shock wave, plasma, high power density). A damaged exit window has a detrimental effect on the ability of the device to provide a sufficiently tight focus at the desired position, which may reduce the efficacy of the treatment process. In particular, if superficial lesions are created above dermis, petechiae (micro-bleeding) will occur due to the micro-rupturing of capillaries, resulting in reduced efficacy, increased side effects and social down time.

There is therefore a need for a system which is able to provide an indication of effectiveness of pulses or an efficacy of treatment.

The invention is defined by the claims.

Examples in accordance with a first aspect of the invention provide a light based tissue treatment device as defined in the independent claims. While in principle all devices will have a light exit window, during use of some devices the light exit window may not need contact with the tissue to be treated. The current invention provides a feedback solution based on the same inventive principle which solution allows estimation of a pulse effectiveness and therewith treatment efficacy for each of the types of devices.

The exit window can take any shape as long as it allows exiting of the pulse light form the device in order to have it enter the tissue. The exit window can be of a lens surface or other optical surface. The light exit window can have a contact surface. The tissue preferably is tissue of a mammal such as hair, skin or organ surface or boundary tissue of e.g. an animal or human being).

The feedback signal can be used to determine whether or not the focal spot is in the tissue. This feedback system is thus able to ensure that sufficient lesions are created by optical breakdown to have its effect (such as e.g. skin rejuvenation) by ensuring that they are created only in the tissue. This enhances the efficacy of the treatment with minimal side-effects and, in case of skin tissue, possible social down time. The feedback can be used to provide improved contact with the tissue and uniform optical coupling, as well as preventing contact window/exit lens damage and tissue damage. This gives improved safety and efficacy of the treatment. A preferred tissue to be treated is skin.

In embodiments, especially when the feedback light or sound is detected from the focal spot, it can be determined whether or not actual LIOB has taken place. This may provide additional certainty in the determination of the pulse effectiveness.

Counting one or more effective pulses within a set of one or more provided pulses provided during treatment or a time period and comparing these with the number of provided pulses provides an indication of effectiveness or efficacy of treatment. This may be done for one pulse per one provided pulse or it may be done for a plurality of provided pulses. A ratio of effective pulses and provided pulses is convenient for indicating the effectiveness or efficacy and this may be indicated by the ratio or a percentage or the like. Multiple sets of pulses may be successive, or they may overlap to provide a running average.

The device may comprise a hydrophone for measuring an acoustic signal. The high energy deposited on the tissue in the focus creates thermal (thermoelastic expansion), optical (plasma spark), and acoustic phenomena. The acoustic signal consists of a characteristic broadband audible acoustic wave, resulting from the supersonic expansion of the generated shock waves, and the expansion of the plasma wave associated to it. The acoustic emission from laser-produced plasmas may for example be detected using a dynamic microphone placed at an approximate distance of a few cms from the plasma. The preferred characteristic acoustic frequency is in the range of the 3 to 16 kHz. This works well for skin tissue.

The feedback system thus preferably comprises a controller for identifying spectral peaks in the hydrophone output which provide an indication of the material in which LIOB has taken place.

The device may comprise an image sensor and an image processor. The focal point can be detected based on a characteristic optical flash (plasma spark) associated with LIOB. Typically the broad spectral range of the characteristic flash is in the wavelength range of 400-1100 nm. The emission spectra from the plasma can be measured using a combination of a spectrometer and an intensified charged coupled device detector (ICCD). Depending on the focal position, the flash spectra exhibits spectral peaks that are characteristic of the material in the focus (glass interface, immersion medium, tissue such as e.g. skin etc.) and can be used as a signature of the focal point and also as an indicator whether LIOB has taken place.

The image processor is thus preferably for identifying spectral peaks in the light received from the tissue which provide an indication of the material in which LIOB has taken place.

The image processor may additionally be adapted to analyze an image captured by the image sensor to determine a quality of contact between the focusing system and the tissue.

In this way, optical analysis can be used to determine both the depth of focus and the quality of optical contact of the system with the tissue.

The quality of the contact can be measured based on the uniformity of specular reflection in the images captured by simple monochrome or RGB cameras. In the case of optimal and uniform coupling, the intensity distribution follows a homogenous Gaussian distribution. Image features and non-uniformities are representative of reduced optical contact quality.

Thus, the image processor may be for identifying non-uniformities in the image captured which are representative of the quality of contact.

The image processor may be adapted to analyze an image captured by the image sensor to determine a level of tissue color change such as e.g. skin redness. In this way, the treatment can be halted if a level of irritation beyond an acceptable threshold is detected. Thus, the feedback system may implement both preventative measures to prevent excessive irritation but also have a safety net which detects when the treatment has resulted in an unacceptable level of irritation.

The device may comprise another feedback system for monitoring a pressure or force applied to the device against the tissue. Preferably there is also provided an output system for giving an indication to the user of the applied pressure or force. Comparison of the monitored pressure or force with a reference pressure or force may be performed in order to indicate whether or not the applied pressure or force is a suitable pressure or force. The pulse provision may be interrupted automatically when the applied pressure or force is below the reference value.

In this way, the user is guided to apply a pressure or force which is suitable to maintain a required contact with the tissue.

In all examples, the feedback system or a controller may be provided that is for reducing the power density of the focused pulsed light beam to a value below a threshold for generating substantial LIOB in air, tissue or other medium if it is determined that the focal spot is outside the tissue (this provides a safety cut-off) or if a particular predetermined efficacy has been reached for a treatment area (this provides an efficient treatment with regard to time). In such case an indication to a user may be given that the predetermined efficacy has been reached.

Reducing the power density can be done by reducing the power of the beam or the quality or extent of focus in the focal spot. Many ways can be used. The feedback system or a controller may be provided for deactivating the light source or dimming the light source or beam provided by it when it is determined that the treatment should stop, because the focal point is determined not to be in the tissue, or there is excessive tissue color change (e.g. skin redness), or there is poor contact detected. This provides a safety cut-off.

Another aspect of the invention provides a light based tissue treatment device comprising:

a light source for providing a pulsed light beam for treating tissue by laser induced optical breakdown of the tissue;

a focusing system for focusing the light beam into a focal spot in the tissue; and a feedback system for a determining a pressure or force applied to the device against the tissue.

The device can comprise an output system for providing the determined pressure or force to a user. Preferably the determined pressure or force is compared to a reference value and the output system provides an indication to the user as to whether or not a suitable pressure or force is being applied.

Another aspect of the invention provides a light based tissue treatment device comprising:

a light source for providing a pulsed light beam for treating tissue by laser induced optical breakdown of the tissue;

a focusing system for focusing the light beam into a focal spot in the tissue;

a feedback system for detecting light received from the tissue comprising an image sensor and an image processor for analyzing an image captured by the image sensor, thereby to determine a quality of contact between the focusing system and the tissue, wherein the image processor is adapted to identify non-uniformities in the image captured which are representative of the quality of contact.

Preferably the device also includes a controller for deactivating the light source or preventing the incident light from reaching the skin when the quality of the contact drops below a threshold, i.e. when the pressure or force drops below a threshold. The controller may operate e.g. a shutter or light beam deflection device for the latter purpose.

Another aspect of the invention provides a light based skin treatment device comprising:

a light source for providing a pulsed light beam for treating tissue by laser induced optical breakdown of the tissue;

a focusing system for focusing the light beam into a focal spot in the tissue; and a feedback system for detecting light received from the skin comprising an image sensor and an image processor, wherein the image processor is adapted to analyze an image captured by the image sensor to determine a level of coloration of the tissue.

Preferably the level of a coloration is a level of skin redness. This relates to e.g. the aspect of analyzing skin redness, as explained above.

In this case, controller may be provided for deactivating the light source or preventing the incident light from reaching the skin when a level of skin redness exceeds a threshold. Again, the controller may operate e.g. shutter or light beam deflection device for implementing the prevention.

The measures outlined above may also be employed, such as analyzing an image captured by the image sensor to determine a quality of contact between the focusing system and the tissue and then deactivating the light source when the quality of contact is determined to be below a threshold level.

The feedback system may also be used for detecting a sound generated by a light source pulse, thereby to determine whether or not the focal spot is in the tissue. In this case, the light source is deactivated when the focal spot is determined not to be in the tissue.

The feedback system discussed above for monitoring a pressure applied to the device against the tissue may also be employed, in which an output system is used for providing an indication to the user as to whether or not a suitable pressure is being applied. In this case, the light source is deactivated when the pressure is determined not to be suitable.

The invention also provides a light based skin treatment method comprising: providing a pulsed light beam for treating tissue by laser induced optical breakdown of the tissue;

focusing the light beam into a focal spot in the tissue; and detecting light received from the tissue and detecting a sound generated by a light source pulse, thereby to determine whether or not the focal spot is in the tissue.

The invention also provides a light based tissue treatment method comprising: providing a pulsed light beam for treating tissue by laser induced optical breakdown of the tissue;

focusing the light beam into a focal spot in the tissue; and sensing a pressure applied to the device against the tissue, and providing an indication to the user as to whether or not a suitable pressure is being applied.

The invention also provides a light based tissue treatment method comprising:

providing a pulsed light beam for treating tissue by laser induced optical breakdown of the tissue;

focusing the light beam into a focal spot in the tissue; and detecting an image of light received from the tissue and analyzing the image to determine a level of tissue coloration such as e.g skin redness.

These methods are non-therapeutic methods, in particular cosmetic methods, for e.g. skin rejuvenation, wrinkle reduction, or hair removal.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a pulsed laser skin treatment device for laser induced optical breakdown of tissue of mammals such as in particular skin tissue. A feedback system is used for detecting a feedback signal from the skin that is caused by LIOB phenomena in the tissue. The feedback signal can comprise light received from the tissue and the feedback system can comprises light sensor or an image sensor and an image processor. In one example, the image processor is adapted to analyze an image captured by the image sensor to determine a level of tissue coloration (e.g. skin redness). In another example, the image captured by the image sensor is used to determine a quality of contact between the focusing system and the tissue. In another example, the feedback system is also for detecting a sound generated by a light source pulse, thereby to determine whether or not the focal spot is in the tissue. In another variation which does not rely upon image sensing, a feedback system is used for monitoring a pressure applied to the device against the tissue, and an output system is used to provide an indication to the user as to whether or not a suitable pressure is being applied.

Before describing the invention in detail, an outline will be given of one example of the type of device to which the invention relates.

Figure 1:
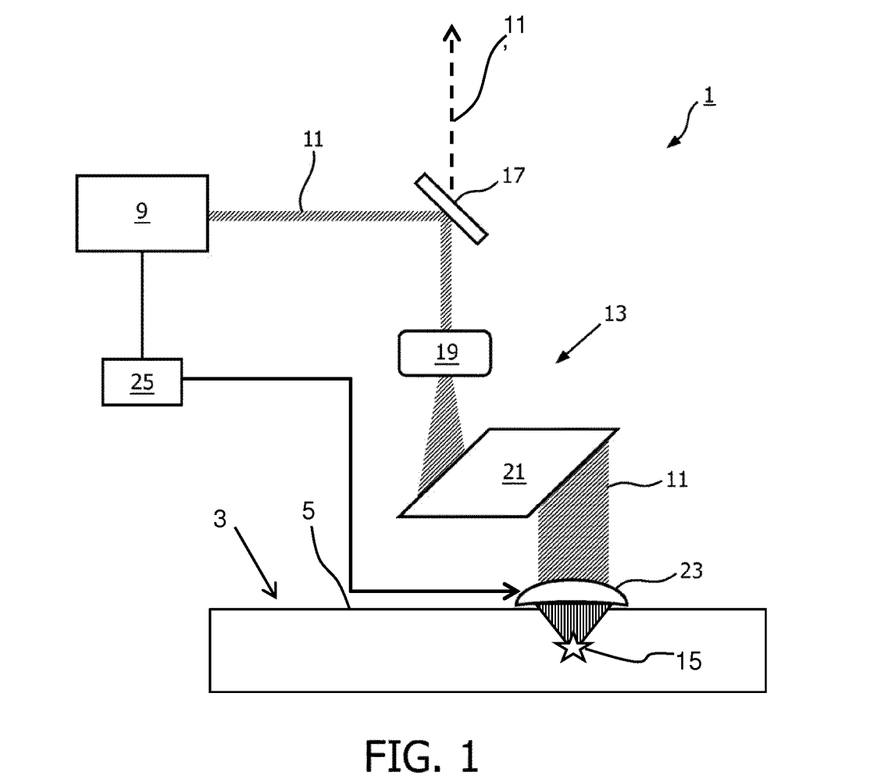
FIG. 1 schematically shows a known LIOB skin treatment device.

FIG. 1 shows a system 1 for treatment of a tissue 3 having a surface 5. In this case the tissue is exemplified by a skin 3, but other tissues can be treated.

The system 1 comprises a light source 9 for generating a laser beam 11 during at least a predetermined pulse time, and it comprises an optical system 13 for focusing the laser beam 11 into a focal spot 15 and for positioning the focal spot 15 in a target position within the skin 3, which is at least partly transparent to the light from the light source 9.

The example of the optical system 13 schematically indicated in FIG. 1 comprises a beam deflection and dichroic beam splitting system 17, an aberration correcting system 19, a beam scanning system 21 and a focusing system 23, which systems may comprise one or more mirrors, prisms, beam splitters, polarizers, optical fibers, lenses, apertures, shutters, etc. For example, the scanning system comprises scanning prisms.

The focusing system has focusing depth selection, beam shaping and focusing and a contact/output window. There is a contour following suspension to maintain contact of the contact/output window.

At least part of the optical system 13 and/or the beam path of the laser beam 11 may be enclosed, e.g. for eye-safety, e.g. comprising opaque tubes and/or one or more optical fibers.

The light source 9 is configured to emit a predetermined number of laser pulses at a predetermined wavelength and with a predetermined pulse duration and repetition rate. The system 1 is configurable such that the target position of the focal spot 15 is beneath the surface of the skin. The dimension of the focal spot 15 and the power of the generated laser beam are such that, in the focal spot 15, the laser beam 11 has a power density, which is above the characteristic threshold value for the skin tissue, above which, for the predetermined pulse time, a laser-induced optical breakdown event occurs.

There may be an articulating arm between the laser source 9 and the beam deflection and dichroic beam splitting system 17. The beam deflection system 17 and subsequent components form part of a hand piece. Because of alignment errors in the mirrors of the articulating arm, the beam may be expanded before entering the articulating arm and then compressed afterwards before beam steering and aberration correction.

The skin 3 comprises multiple layers with different optical properties. The epidermis is composed of the outermost layers and forms a waterproof protective barrier. The outermost layer of the epidermis is the stratum corneum which, due to its microscopic fluctuations in roughness, impedes the coupling of light between the device 1 and the skin 3. For this reason, a coupling fluid is preferably provided between the focusing system and the tissue, with a refractive index which aims to match that of the tissue and/or an exit lens/window of the focusing system.

Underneath the epidermis, the dermis is situated. The dermis comprises the collagen fibers at which the skin treatment is aimed.

The purpose of the skin treatment is to create the focus 15 of the pulsed laser beam 11 in the collagen of the dermis in order to create microscopic lesions which result in new collagen formation.

The light source 9 is controllable with an optional controller 25, which may provide a user interface. Also, one or more parts of the optical system 13 may be controllable with an optional controller (not shown), which may be integrated with a light source controller 25 to control one or more properties of the target position and/or the focal spot.

Laser beam focusing parameters may be determined by appropriate settings of a beam shaping and/or focusing system, e.g. by adjustment of the numerical aperture of the focusing system. Suitable values for the numerical aperture NA of the focusing system may be chosen from a range 0.05<NA<nm, wherein nm is the index of refraction of the medium for the laser wavelength, during operation.

A suitable light source comprises a Q-switched Nd:YAG laser emitting laser pulses at a wavelength of about 1064 nm with a pulse duration of about 5-10 ns, although other lasers, e.g. a Nd:Cr:Yag 3-level laser and/or diode lasers may be used as well. A 1064 nm laser is preferably used for treatment because of the relative low absorption and scattering inside the skin and thereby providing large penetration depth.

The beam deflection and dichroic beam splitting system 17 comprises a dichroic beam splitter which reflects the laser light but passes visible wavelength light. Thus, received visible wavelength light from the skin 3 is captured by the optical system and is provided as a feedback signal 11' which can be used for controlling the system either manually or automatically.

The focusing depth provided by the focusing system 23 is preferably adjustable.

Figure 2:
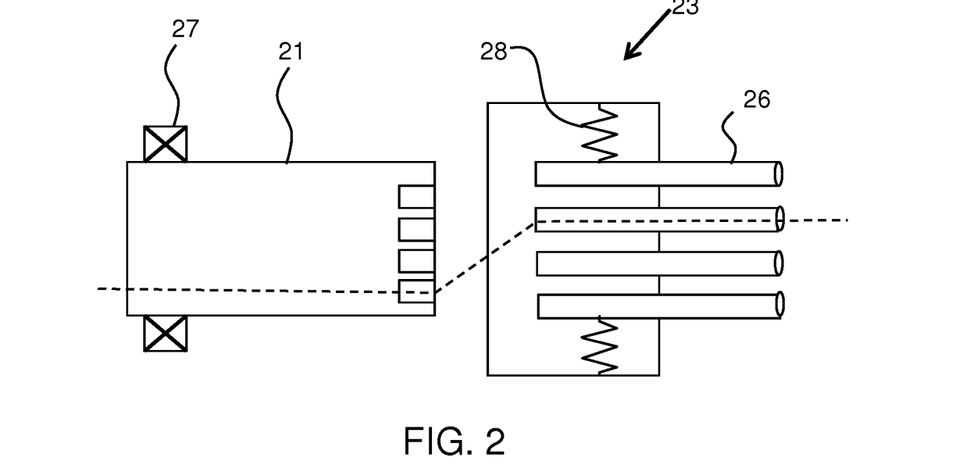
FIG. 2 shows a known way to implement focal depth control.

FIG. 2 shows a known way to implement such adjustment. The focusing system 23 comprises a set of output windows 26 each with a different focus depth, and an optical path is provided to one of the output windows by the scanner motor 27, which rotates the scanning system 21. The output windows 26 are held by a contour following suspension 28. The output windows are thus arranged around a circular path, and a notch system provides positioning with respect to the scanning system 21. There may be four output windows, and thus four lens sets each separately spring loaded to provide contour following.

The scanning system 21 is used to scan the focus across an area of skin.

One example of laser that may be used in the system of FIG. 1 has a maximum repetition frequency of 1000 Hz, and a typical treatment regime uses a lesion pitch of 200 µm, resulting in a typical maximum scan speed of 200 mm/s. This scan speed rules out any manual-scanning-only options because of lack of control when applying these scanning speeds by hand.

Additionally, any start-stop scanning system will be severely challenged to reach this scanning speed over a short distance of acceleration, leading to mechanical vibrations and ineffective use of the capacity of the laser. A more easily controlled slower scanning speed will significantly increase the treatment time for large surface areas. To overcome this challenge a continuous motion scanning may be used on the basis of rotary motion, which can easily achieve these scan speeds and does not suffer from strong vibrations and ineffective use of the laser capabilities.

For this purpose a rotating prism may be used.

A first possible prism design comprises a rhomboid. Two opposite parallel end faces function as total internal reflection faces. They are at 45 degrees to the incident light direction. The two internal reflections in the prism provide a lateral shift of an incident beam, so that exit beam is parallel but laterally shifted relative to the input beam. By rotating the prism about an axis perpendicular to the lateral shift direction, and therefore parallel to the incident beam direction a circular path is swept by the output beam. The rotation is about the axis of the input beam. The radius of the circle swept is the length of the rhomboid. Rhomboid prisms can be manufactured with anti-reflection coatings on the faces where required.

A second possible prism design is a dove prism. The two end faces function as refraction interfaces, and the bottom face functions as a total internal reflection face. The end faces are at 45 degrees to the incident light. The two refractions and the single total internal reflection in the prism again provide a lateral shift of an incident beam, so that exit beam is parallel but laterally shifted relative to the input beam. By rotating the prism about an axis perpendicular to the lateral shift direction, and therefore parallel to the incident beam direction, a circular path is swept by the output beam. The rotation is about the axis of the input beam. The amount of beam translation depends on the position of the incident beam relative to the input surface of the dove prism and on the size of the prism. The prism is rotated around the chief incident ray. Anti-reflection coatings may again be added on the angled surfaces to reduce losses by reflection.

The rotating prism is mechanically balanced to avoid vibration. A prism mount is suspended on ball bearings and connects directly to a motor rotor so as to minimize the influence of the aberration correction settings on the effective numerical aperture of the focused light.

This invention relates to feedback systems for controlling the system to prevent damage to the exit window of the focusing system 23 and/or to stop or prevent skin irritation.

A first aspect relates to a feedback system which combines optical and acoustic analysis, in order to detect the focus depth at which LIOB is occurring. The feedback system then enables the laser to be switched off if the focus is not in the skin. This is based on the differences in the wavelength spectrum of a visible flash (plasma spark) and acoustic frequencies of the signal generated during LIOB, which show significant differences depending on the medium in which it occurs, such as air, the lens, the coupling medium and the skin.

The emission spectra can be measured using a combination of a spectrometer and an intensified charged coupled device detector (ICCD). Depending on the focal position, the flash spectra exhibits spectral peaks that are characteristic of the material in the focus (glass interface, immersion medium, skin etc.) and can be used as a signature of the focal point and also as an indicator whether LIOB has taken place.

For instance, in the absence of LIOB, the detector records a flat background spectrum without any spectral features. As an example, the characteristic peaks occurring around 212.4 nm (Si) and 589 nm (Na) can be used for confirming that LIOB is occurring in the glass interface and skin respectively. Other spectral peaks can also be used as indicator of the material. For irradiance threshold below the optical breakdown, flashes without LIOB can also be measured and the differences in the spectral characteristics of the optical flash with and without optical breakdown can also be used a signature.

Figure 3:
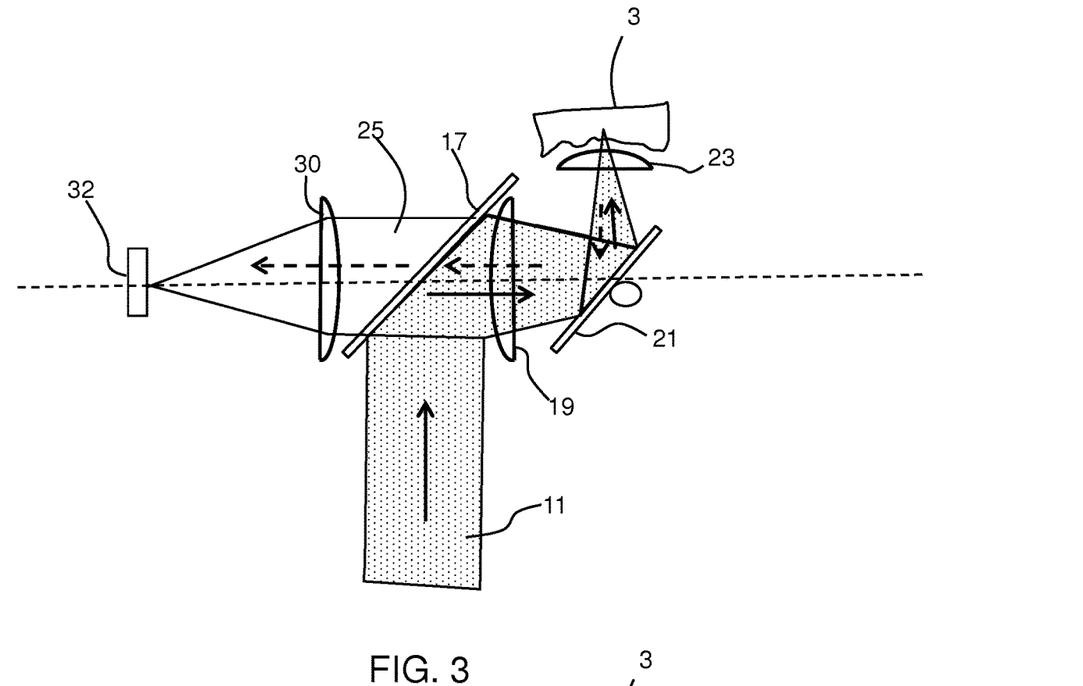
FIG. 3 shows a device with a first example of feedback system.

FIG. 3 shows a first example, based on a confocal system for detecting focus depth.

The same components are given the same reference numbers as in FIG. 1. The aberration correction system 19 comprises an aspheric lens and the focusing system 23 comprises a lens which functions as microscope objective. The visible light optical feedback signal 25 transmitted through the dichroic beam splitter 17 is focused by a plane convex lens 30 onto an image sensor 32 for example a CCD chip.

This arrangement provides confocal detection of the focusing depth to prevent LIOB outside the skin and to determine the focusing depth inside the skin.

The optical paths of the confocal microscope formed by lenses 30 and 23 (illumination and detection) and the LIOB treatment beam are coupled together by the dichroic beam splitter 17. The confocal microscope makes depth resolved images of the focal position and thus enables a verification of the treatment depth. This verification is carried out using image processing of the image captured by the image sensor, and the verification is used by the controller 25 to activate or deactivate the laser 9.

Figure 4:
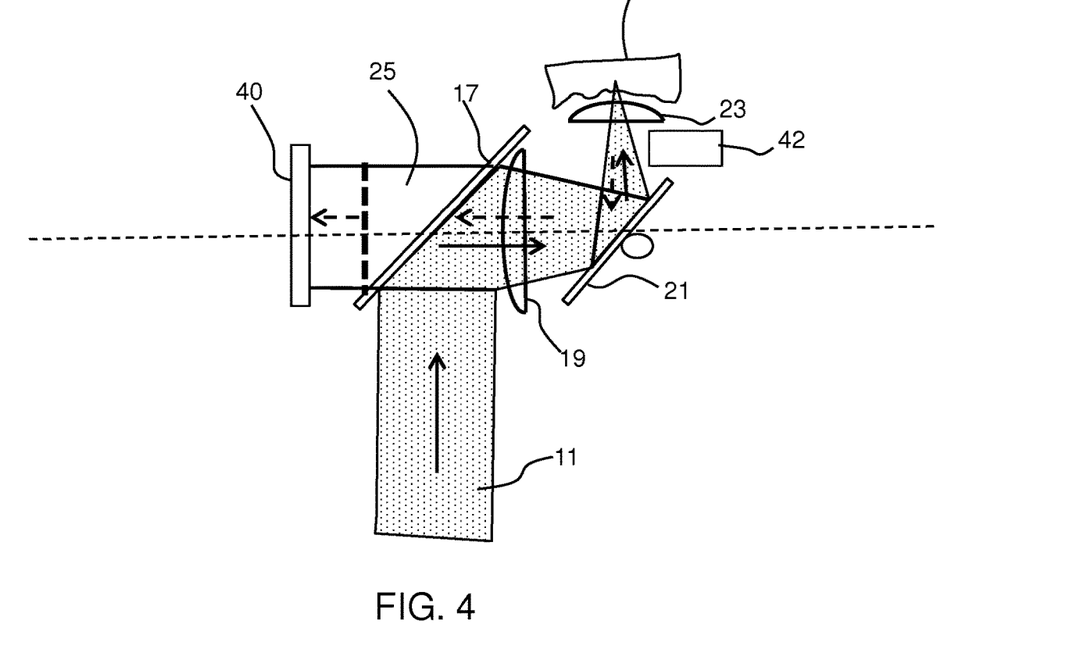
FIG. 4 shows a device with a second example of feedback system.

FIG. 4 shows a second example, based on providing a feedback system based on both light and sound.

The same components are given the same reference numbers as in FIG. 3. An image sensor is no longer needed, and instead there is a photodiode or photodiode array 40 and optionally an associated diffraction grating for analyzing a spectrum of the visible light 25, rather than an image formed. A needle hydrophone 42 enables analysis of a spectrum of a sound wave.

The visible light flash and acoustic signal generated during LIOB exhibits different spectral and acoustic characteristics in air, in the coupling medium and in the skin. During the occurrence of the LIOB, the visible flash can be recorded by the photodiode 40 (or by a grating) and the acoustic signal is recoded by means of the hydrophone. The combined detection of the flash and the acoustic signal enables the focusing depth to be determined.

The visible light received from the skin is the result of a photomechanical mode of interaction which occurs in Laser induced optical breakdown. It involves the massive generation of free electrons. The process is termed 'electron avalanche growth' or the 'inverse Bremsstrahlung effect'. The formation of plasma results in a white light continuum that has little intensity variation as a function of wavelength. This light is caused by Bremsstrahlung and recombination radiation from the plasma as free electrons and ions recombine in the cooling plasma.

Instead or as well as determining a focal depth, the system of FIG. 3 may be used to analyze the quality of the optical coupling between the skin and the output lens of the focusing system 23. If the optical coupling is not effective, optical breakdown can occur in the air or in the exit surface of the lens, leading to lens and skin damage.

This analysis of the optical coupling may be achieved based on image processing of the image captured by the image sensor 32.

The quality of the contact can be measured based on the uniformity of specular reflection in the images captured by simple monochrome or RGB cameras. In the case of optimal and uniform coupling, the intensity distribution follows a homogenous Gaussian distribution. Larger amounts of image features such as the size of intensity spots, number of spots, the size of the largest spot etc. can be derived from these images after thresholding and these features can be used as indictors of non-optimal coupling.

The system of FIG. 3 may also be modified by removing the image sensor 32 and lens 30 and instead providing an output window to enable visual inspection by a user of the system. The user can then visually inspect the skin contact appearance at each laser flash. Again, this will be visible as imperfections such as image spots.

A further option for detecting the skin contact quality is to use a spring-loaded focusing lens system to provide contour following, with feedback of a measured load. The complete optical system is spring loaded so that the optical paths between optical components are preserved.

Figure 5:
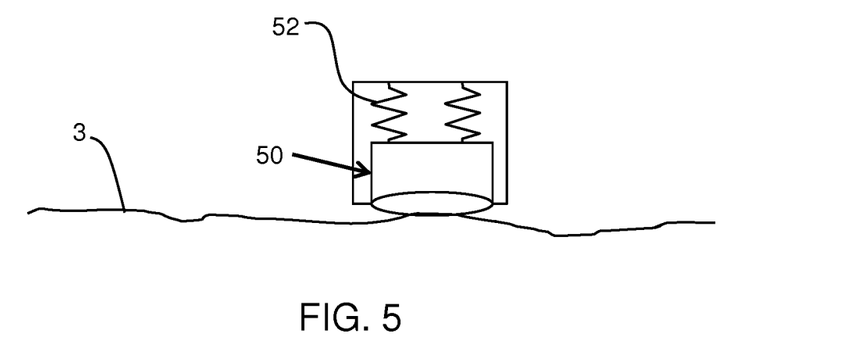
FIG. 5 shows a device with a third example of feedback system.

FIG. 5 shows an optical system 50 including at least the final objective lens which is spring loaded by springs 52 to enable the device to follow the contour of the skin 3. This allows seamless tracking of the curved skin surface while scanning.

Feedback based on the load in the system is used to control the laser activation. A set of reference load values may be used to ensure optimal contact and thereby act as a reference for the spring system.

Feedback is then provided to enable the user to maintain the load within the desired range of load levels. This range of load levels is preferably between (and therefore excludes) full spring extension (zero load) and maximum spring compression (maximum load) since both of these are inappropriate to maintain good contact.

The output to the user may be provided on a screen of the system, or it may be sent as a wireless signal to a smart phone, watch, or other nearby device with wireless connectivity. The instructions to the user may be audible, for example with a warning sound when the pressure being applied is too low or too high, and/or a visual output may be provided.

At least two contact points are defined in close proximity to ensure proper contour following of both small local skin features as well as larger global skin contours and features.

As mentioned above, if superficial lesions are created above the dermis, petechiae (micro-bleeding) may occur. This may arise as a result of poor optical contact between the focusing system and the skin, or resulting from on damage to the focusing system. The feedback approaches above aim to prevent such damage or prevent laser operation when there is poor optical contact.

An alternative (or additional) approach is to detect the resulting redness of the skin, and thereby halt treatment as soon as early signs of skin damage are evident.

The feedback system is then based measuring the erythema (skin redness). This feedback can then optimize the efficacy of the LIOB based treatment for skin rejuvenation by disabling the device after recording an increase in erythema with respect to a baseline redness measured before the treatment. This reduces side-effects and social down time.

The threshold value for the increase in erythema can be fine-tuned depending on the required coverage and severity of the side effect and subjective pain perception related to the LIOB treatment. The suitable threshold may vary between different subjects, and even for the same subject at different times.

Quantitative determination of erythema with respect to the baseline value is an indication of effectiveness of LIOB based skin treatment and may be used to confirm that the treatment was effective and that the required skin healing response is expected to take place leading to skin rejuvenation effects.

Thus, instead of or as well as determining a focal depth and/or analyzing the quality of a skin contact, the system of FIG. 3 may be used to analyze the level of skin redness.

The system of FIG. 3 may be modified by removing the image sensor 32 and lens 30 and instead providing an output window to enable visual inspection by a user of the system. The user can then visually inspect the skin redness at each laser flash.

However, the preferred option is to use the image sensor 32 for automatic analysis of the spectral content of the captured image using image processing of the image captured by the image sensor 32. In particular, changes in the spectral content, with an increase in red component, is detected when compared to an initial color at the beginning of the treatment. The image sensor may instead comprise a spectrophotometer.

In general, LIOB treatment leads to mild erythema immediately after treatment, and the severity increases for around 10 minutes. Erythema then fades and is no longer visible 30 minutes after treatment. The appearance of mild erythema is an indication that the treatment is effective and skin healing response was expected to take place. However, it should not be allowed to pass a threshold of severity.

The image sensing may use high resolution photography, but low resolution photography using a low cost sensor is also sufficient to detect a red content in the image. Spectrophotometry may be performed, or image processing of a CCD image may be used.

Figure 6:
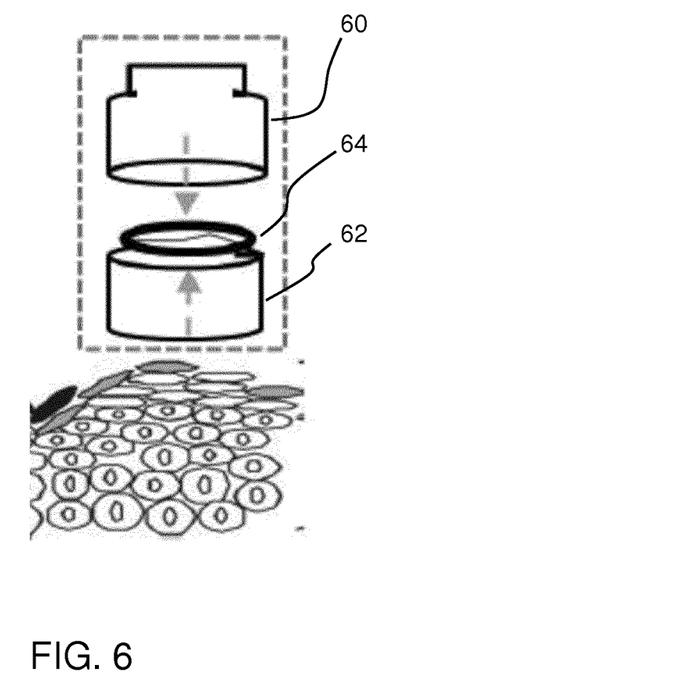
FIG. 6 is used to explain an optical feedback system.

FIG. 6 shows the image analysis system which comprises a high resolution camera 60 with built in image processing algorithms for quantitative cell analysis.

The camera 60 is integrated with an additional module consisting of a detachable mount 62. The camera unit consists of a LED illumination ring 64 and performs spatially resolved detection of backscattered light.

The increase in erythema is compared with a reference look-up table showing values corresponding to the treatment coverage area and specifying the limit of acceptable redness for the subject. An initial baseline measurement is used as a calibration reference.

The contact pressure feedback system as described above may also be employed.

To use the system, an initial baseline skin color is recorded by the system, prior to any application of a mechanical redness provocation (tape stripping or other). This skin color is recoded from a skin area to be treated.

A comparison of an irritated skin or erythema (increase in redness) with the baseline skin may also be made before the treatment, so that the way a particular subject reacts to treatment can be recorded.

The LIOB treatment is then carried out.

The skin redness is recorded after the first treatment. A comparison is then made with respect to the desired erythema threshold, which in turn depends on the required treatment coverage area and acceptable subjective pain perception. The subject indicates their discomfort threshold by providing pain perception information during treatment and also by visual assessment of the irritated skin afterwards.

If the skin redness in the treated area is greater than the baseline skin color and has reached the threshold the treatment is stopped, otherwise the LIOB treatment is continued.

As mentioned above, Nd:YAG lasers with emission at 1064 nm may be used, but also or Er:YAG lasers with emission at 1645 nm may be used for laser induced optical breakdown (LIOB).

The skin treatment may comprise a hair removal shaving process. During use, the focusing system 23 is moved over the skin surface to be shaved. The focusing system forms an exit window for allowing the light beam to leave the device. The focusing system then forms an optical blade.

The skin treatment may comprise skin rejuvenation device for reducing wrinkles that may appear in human skin as a result of normal aging processes. During use, the focusing element is pressed onto or kept close to the skin to be treated. The exit window formed by the focusing system is held parallel to the skin and the light beam leaves the exit window and enters the skin in a direction substantially perpendicular to the skin surface.

In both examples, an immersion fluid may be provided between the focusing system and the skin surface. Preferably, an immersion fluid is used with a refractive index close to the refractive index of the skin contact lens of the focusing system 23 and the skin or hair where the LIOB is to occur. For this purpose, fluids with a refractive index of about 1.4 to about 1.5 are suitable. Also water, although having a somewhat lower refractive index of 1.33, may for some devices and applications be a suitable immersion fluid.

The system of FIG. 1 has one particular set of optical components between the laser and the focusing system. However, this arrangement is not intended to be limiting. The feedback system of the invention may be used in different system configurations with a smaller or greater number of components.

In summary, a pulsed laser skin treatment device is for laser induced optical breakdown of hair or skin tissue. A feedback system is used for detecting a feedback system based on light and/or sound/and/or contact force or pressure. The feedback signal is used to determine whether a pulse was in the tissue or outside the tissue. With these data an effectiveness of the treatment can be determined which can be provided to a user.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A device for treating tissue of a subject, the device comprising:
   a light source, the light source providing pulsed light beams,
   a focusing system, wherein the focusing system is arranged to focus the pulsed light beams into a focal spot that can be positioned in the tissue; and
   a feedback system,
   wherein the feedback system is arranged to detect a feedback signal,
   wherein the feedback signal comprises light and/or sound generated by laser induced optical breakdown of a material caused by the pulsed light beams,
   wherein the feedback system is arranged to determine, based on the feedback signal whether or not the focal spot was in the tissue during the pulse,
   wherein the feedback system is arranged to count a number of effective pulses for a number of pulses of the pulsed light beam,
   wherein the effective pulses comprise pulses that are determined to have caused laser induced optical breakdown of the tissue at the focal spot, and
   wherein the feedback system is arranged to compare the number of effective pulses with the number of pulses of the pulsed light beam to assess an effectiveness of the treating of the tissue.

2. The device as claimed in claim 1, wherein the feedback system is arranged to determine, based on the feedback signal, whether laser induced optical breakdown occurred for each pulse of the pulsed light beams.

3. The device as claimed in claim 1, wherein comparing the number of effective pulses comprises determining a ratio of the number of effective pulses and the number of pulses of the pulsed light beam.

4. The device as claimed in claim 1, further comprising a user interface, wherein the user interface provides an indication representative of the effectiveness.

5. The device as claimed in claim 1, comprising a hydrophone for determining the sound,
   wherein the feedback system is arranged to identify spectral peaks in the hydrophone output,
   wherein the spectral peaks provide an indication of the material in which laser induced optical breakdown has taken place.

6. The device as claimed in claim 1, further comprising:
   a sensor; and
   a processor circuit,
   wherein the sensor is arranged to detect light and provide the feedback signal,
   wherein the processor circuit is arranged to process the feedback signal.

7. The device as claimed in claim 6, wherein the processor circuit is arranged to analyze the light detected.

8. The device as claimed in claim 6, wherein the processor circuit is arranged to analyze the light detected in an image captured by an image sensor to determine a level of coloration of the tissue.

9. The device as claimed in claim 1, further comprising:
   an image sensor; and
   an image processor circuit,
   wherein the image processor circuit is arranged to identify spectral peaks in the light,
   wherein the spectral peaks provide an indication of the material in which a laser induced optical breakdown has taken place.

10. The device as claimed in claim 1, wherein the feedback system is arranged to determine a contact force or contact pressure.

11. The device as claimed in claim 10, further comprising an output system, wherein the output system is arranged to provide an indication to the user as to whether or not the contact force or pressure is being applied that exceeds a reference pressure.

12. The device as claimed in claim 1, further comprising a user interface,
   wherein the user interface provides an indication representative of the treatment efficacy to a user of the device.

13. The device of claim 1, wherein the feedback system determines a type of the material in which the laser induced optical breakdown occurred to determine whether or not the focal spot was in the tissue.

14. The device of claim 13, wherein the feedback system determines the type of the material based on spectral characteristics of the feedback signal.

15. The device of claim 1, wherein the feedback system determines a quality of optical coupling of the light source and the tissue based on spectral characteristics of the feedback signal.

* * * * *